US012678237B2

(12) United States Patent
Azizian

(10) Patent No.: US 12,678,237 B2
(45) Date of Patent: Jul. 14, 2026

(54) RECONFIGURABLE DISPLAY IN COMPUTER-ASSISTED TELE-OPERATED SURGERY

(71) Applicant: Intuitive Surgical Operations, Inc., Sunnyvale, CA (US)

(72) Inventor: Mahdi Azizian, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 928 days.

(21) Appl. No.: 17/677,253

(22) Filed: Feb. 22, 2022

(65) Prior Publication Data

US 2022/0175470 A1    Jun. 9, 2022

Related U.S. Application Data

(63) Continuation of application No. 16/347,298, filed as application No. PCT/US2017/060000 on Nov. 3, 2017, now abandoned.

(Continued)

(51) Int. Cl.
*A61B 34/00* (2016.01)
*A61B 34/10* (2016.01)
(Continued)

(52) U.S. Cl.
CPC .............. *A61B 34/25* (2016.02); *A61B 34/30* (2016.02); *A61B 34/35* (2016.02); *A61B 90/37* (2016.02);
(Continued)

(58) Field of Classification Search
CPC ... A61B 34/30; A61B 34/25; A61B 2034/254; A61B 2034/252
See application file for complete search history.

(56) References Cited

U.S. PATENT DOCUMENTS 7,525,309 B2    4/2009 Sherman et al.
7,794,396 B2    9/2010 Gattani et al.
(Continued)

FOREIGN PATENT DOCUMENTS

CN    102326163 A    1/2012
CN    102592484 A    7/2012
(Continued)

OTHER PUBLICATIONS

Extended European Search Report for Application No. EP17866484.3 mailed on Jun. 29, 2020, 07 pages.
(Continued)

*Primary Examiner* — Keith M Raymond
*Assistant Examiner* — Ashish S. Jasani
(74) *Attorney, Agent, or Firm* — Artegis Law Group, LLP

(57) ABSTRACT

The technology described in this document can be embodied in a method that includes operating a surgical system to perform a surgical process, the surgical system including a display device, and receiving, at one or more processing devices, data from multiple data sources. The method also includes determining a current phase of the surgical process, and displaying, on the display device, visual representations corresponding to the data from a first set of the multiple data sources in a first arrangement within a display region of the display device. At least one of the first set of the multiple data sources and the first arrangement is associated with the current phase of the surgical process.

22 Claims, 8 Drawing Sheets

Related U.S. Application Data

(60) Provisional application No. 62/417,493, filed on Nov. 4, 2016.

(51) Int. Cl.

| | | |
|---|---|---|
| *A61B 34/30* | (2016.01) | |
| *A61B 34/35* | (2016.01) | |
| *A61B 90/00* | (2016.01) | |

(52) U.S. Cl.
CPC ... *A61B 2034/107* (2016.02); *A61B 2034/252* (2016.02); *A61B 2034/254* (2016.02); *A61B 2034/258* (2016.02); *A61B 2090/373* (2016.02); *A61B 2090/374* (2016.02); *A61B 2090/3762* (2016.02); *A61B 2090/378* (2016.02)

(56) References Cited

U.S. PATENT DOCUMENTS

| | | | |
|---|---|---|---|
| 8,280,483 | B2 | 10/2012 | Zhu et al. |
| 9,161,817 | B2 | 10/2015 | Olson et al. |
| 9,468,413 | B2 | 10/2016 | Hall et al. |
| 2007/0167703 | A1 | 7/2007 | Sherman et al. |
| 2008/0183074 | A1* | 7/2008 | Carls ..................... A61B 6/506 |
| | | | 600/429 |
| 2008/0269596 | A1 | 10/2008 | Revie et al. |
| 2013/0116828 | A1 | 5/2013 | Krause et al. |
| 2013/0345718 | A1 | 12/2013 | Crawford et al. |
| 2014/0005484 | A1 | 1/2014 | Charles |
| 2014/0148818 | A1 | 5/2014 | Komuro et al. |
| 2014/0168266 | A1 | 6/2014 | Kimura |
| 2014/0195051 | A1 | 7/2014 | Bonin et al. |
| 2014/0337794 | A1* | 11/2014 | Vranjes .................. G06F 9/451 |
| | | | 715/800 |
| 2016/0015471 | A1* | 1/2016 | Piron ..................... A61B 1/045 |
| | | | 600/424 |
| 2016/0143699 | A1 | 5/2016 | Tanji |
| 2017/0035517 | A1 | 2/2017 | Geri et al. |
| 2018/0005418 | A1* | 1/2018 | Kim ..................... G06T 11/206 |
| 2019/0000585 | A1 | 1/2019 | Kokubo et al. |
| 2019/0254757 | A1 | 8/2019 | Piron et al. |
| 2019/0254759 | A1 | 8/2019 | Azizian |

FOREIGN PATENT DOCUMENTS

| | | |
|---|---|---|
| CN | 104769943 A | 7/2015 |
| CN | 105556534 A | 5/2016 |
| KR | 20140144992 A | 12/2014 |

OTHER PUBLICATIONS

International Search Report and Written Opinion for Application No. PCT/US2017/060000, mailed on Mar. 27, 2018, 21 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

400

460

700

710

Operate a surgical system to perform a surgical process

720

Receive data from multiple sources

730

Determine a current phase of the surgical process

740

Display visual representations corresponding to the data from a first set of multiple sources in a first arrangement within a display region of the display device

RECONFIGURABLE DISPLAY IN COMPUTER-ASSISTED TELE-OPERATED SURGERY

CROSS REFERENCE TO RELATED APPLICATIONS

This application is a continuation of and claims the benefit of priority to U.S. patent application Ser. No. 16/347,298, filed May 3, 2019, which is a U.S. National Stage Application under 35 U.S.C. § 371 and claims the benefit of International Patent Application No. PCT/US2017/060000, filed on Nov. 3, 2017, which claims the benefit of U.S. Provisional Application No. 62/417,493, filed Nov. 4, 2016. The disclosures of the prior applications are considered part of and are incorporated by reference in the disclosure of this application.

TECHNICAL FIELD

This disclosure relates to devices and methods for minimally invasive computer-assisted tele-operated surgery.

BACKGROUND

Minimally invasive tele-surgical systems for use in surgery are being developed to increase a surgeon's dexterity as well as to allow a surgeon to operate on a patient from a remote location. Tele-surgery is a general term for surgical systems where the surgeon uses some form of remote control, e.g., a servomechanism, or the like, to manipulate surgical instrument movements rather than directly holding and moving the instruments by hand. In such a tele-surgery system, the surgeon is provided with an image of the surgical site at the remote location. The surgeon performs the surgical procedures on the patient by manipulating master control input devices, which in turn control the motion of robotic instruments.

SUMMARY

In one aspect, this document features a method that includes operating a surgical system to perform a surgical process, the surgical system including a display device, and receiving, at one or more processing devices, data from multiple data sources. The method also includes determining a current phase of the surgical process, and displaying, on the display device, visual representations corresponding to the data from a first set of the multiple data sources in a first arrangement within a display region of the display device. At least one of the first set of the multiple data sources and the first arrangement is associated with the current phase of the surgical process.

In another aspect this document features a surgical system that includes a display device and one or more processing devices. The one or more processing devices are configured to operate the surgical system to perform a surgical process, and receive data from multiple data sources. The one or more processing devices are also configured to determine a current phase of the surgical process, and display, on the display device, visual representations corresponding to the data from a first set of the multiple data sources in a first arrangement within a display region of the display device. At least one of the first set of the multiple data sources and the first arrangement is associated with the current phase of the surgical process.

In another aspect, this document features one or more machine-readable non-transitory storage devices encoded with machine-readable instructions configured to cause one or more processing devices to perform various operations. The operations include operating a surgical system to perform a surgical process, the surgical system including a display device, and receiving, at one or more processing devices, data from multiple data sources. The operations also include determining a current phase of the surgical process, and displaying, on the display device, visual representations corresponding to the data from a first set of the multiple data sources in a first arrangement within a display region of the display device. At least one of the first set of the multiple data sources and the first arrangement is associated with the current phase of the surgical process.

Implementations of the above aspects may include one or more of the following. A new phase of the surgical process may be determined, and at least one of the first set of the multiple data sources and the first arrangement may be updated in response to determining the new phase of the surgical process. Updating the at least one of the first set of the multiple data sources and the first arrangement can be based on a user preference record for a current user of the surgical system. Updating the at least one of the first set of the multiple data sources and the first arrangement can be based on a predetermined safety profile for the surgical system. User-input indicative of adjustments to one or more of the visual representations may be received, and the display device may be updated in accordance with the adjustments. A user-profile may also be updated in accordance with the adjustments. The user-profile can be stored at a storage location and be made accessible to other users. The multiple data sources can include at least two of: an endoscope, an ultrasound imaging device, a computed tomography (CT) imaging device, a nuclear imaging device, a radiography imaging device, and a magnetic resonance imaging (MRI) device. The multiple data sources can include at least one of: (i) a computing device generating one or more of an image, text, interactive graphics, or a graphical user interface (GUI), and (ii) a storage device providing one or more pre-stored images or videos. Determining the current phase can be based on a user-input indicative of the current phase. Determining the current phase can be based on an image analysis process executed on the data from at least one of the multiple data sources. The data from one or more of the multiple data sources can include positional information with respect to a common reference frame. Displaying the visual representations can include overlaying a first visual representation on a second visual representation, wherein the first visual representation is registered with respect to the second visual representation based on the common reference frame. The first arrangement can be determined based on a user profile loaded prior to commencement of the surgical process. The user profile can identify an individual performing the surgical process, and include user-preferences of the individual regarding organization of the visual representations corresponding to the data from the multiple data sources during different phases of the surgical process. The display device can include multiple screens.

In another aspect, this document features a method for controlling configurability of visual representations of data from multiple data sources on a display device during a surgical process. The method includes receiving data from the multiple data sources, displaying, on the display device, visual representations corresponding to the data from at least a subset of the multiple data sources at locations determined for each of the visual representations, and receiving, via an input device, user-input indicative of adjustments to one or more of the visual representations. The method also includes determining that at least a portion of the adjustments is in violation of a predetermined safety condition associated with the corresponding visual representation, and in response, generating a control signal configured to alert a user of the violation.

In another aspect, this document features a surgical system that includes a display device and one or more processing devices. The one or more processing devices are configured to receive data from multiple data sources, and display, on the display device, visual representations corresponding to the data from at least a subset of the multiple data sources at locations determined for each of the visual representations. The one or more processing devices are also configured to receive, via an input device, user-input indicative of adjustments to one or more of the visual representations, determining that at least a portion of the adjustments is in violation of a predetermined safety condition associated with the corresponding visual representation, and responsive to determining the violation, generating a control signal configured to alert a user of the violation.

In another aspect, this document features one or more machine-readable non-transitory storage devices encoded with machine-readable instructions configured to cause one or more processing devices to perform various operations. The operations include receiving data from the multiple data sources, displaying, on the display device, visual representations corresponding to the data from at least a subset of the multiple data sources at locations determined for each of the visual representations, and receiving, via an input device, user-input indicative of adjustments to one or more of the visual representations. The operations also include determining that at least a portion of the adjustments is in violation of a predetermined safety condition associated with the corresponding visual representation, and in response, generating a control signal configured to alert a user of the violation.

Some or all of the embodiments described herein may provide one or more of the following advantages. In some cases, visual representation of data from multiple data sources can be displayed on a console of a surgical system based on user-preferences. In some cases, the display preferences of an individual (e.g., a senior surgeon) may be saved as a profile, and later used by other individuals (e.g., junior surgeons, medical students etc.). The display preferences may be specific to phases of surgery, and may be automatically loaded upon detection of corresponding phases. By allowing for overlaying images from different sources (possibly warped and registered with one another), and providing a user control over the locations of the various images, the technology described herein may allow for improved user experience for surgeons performing minimally invasive robotic surgery (also referred to herein as minimally invasive surgery (MIS)). In some cases, virtual proctoring tools (also referred to as ghost tools) may be overlaid on images to allow a surgeon to rehearse a surgical procedure before using actual tools to perform the procedure. Various safety protocols may govern the location and configuration of the images from different sources, for example, to guard against a surgeon accidentally missing important information. This in turn may increase patient safety by reducing chances of human errors that may otherwise affect MIS.

DETAILED DESCRIPTION

This document describes technology that, in some cases, improves visualization of surgical sites and anatomical parts during image-guided surgical processes such as minimally invasive robotic surgery (also referred to herein as minimally invasive surgery (MIS)). For example, the technology allows for configuring locations of images from various sources on a display device associated with a surgeon's console. This may be done manually, for example, in accordance with the preferences of the surgeon as indicated via a user-input, or automatically, for example, based on pre-stored preferences, and/or based on detecting a phase of the surgery. In some implementations, the technology may allow for various types of configurability (e.g., overlaying images on one another, minimizing or removing a feed from a particular image source, or concurrently displaying feeds from multiple data sources) that may in turn allow a surgeon to perform a surgery with increases effectiveness. In addition, the configurability may be governed using safety protocols aimed at reducing the possibility of a surgeon missing useful information. For example, safety protocols may prevent an endoscope image from being configured to a size less than a threshold size, or lock certain displays from being removed from the console.

Aspects of the invention are described primarily in terms of an implementation using a da Vinci® Surgical System, commercialized by Intuitive Surgical, Inc. of Sunnyvale, California Examples of such surgical systems are the da Vinci® Xi™ Surgical System (Model IS4000) and the da Vinci® Si™ HD™ Surgical System (Model IS3000). It should be understood that aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are described for illustrative purposes, and are not to be considered as limiting the scope of the inventive aspects disclosed herein. As applicable, inventive aspects may be embodied and implemented in both relatively smaller, hand-held, hand-operated devices and relatively larger systems that have additional mechanical support, as well as in other embodiments of computer-assisted tele-operated medical devices.

Figures 1, 2:
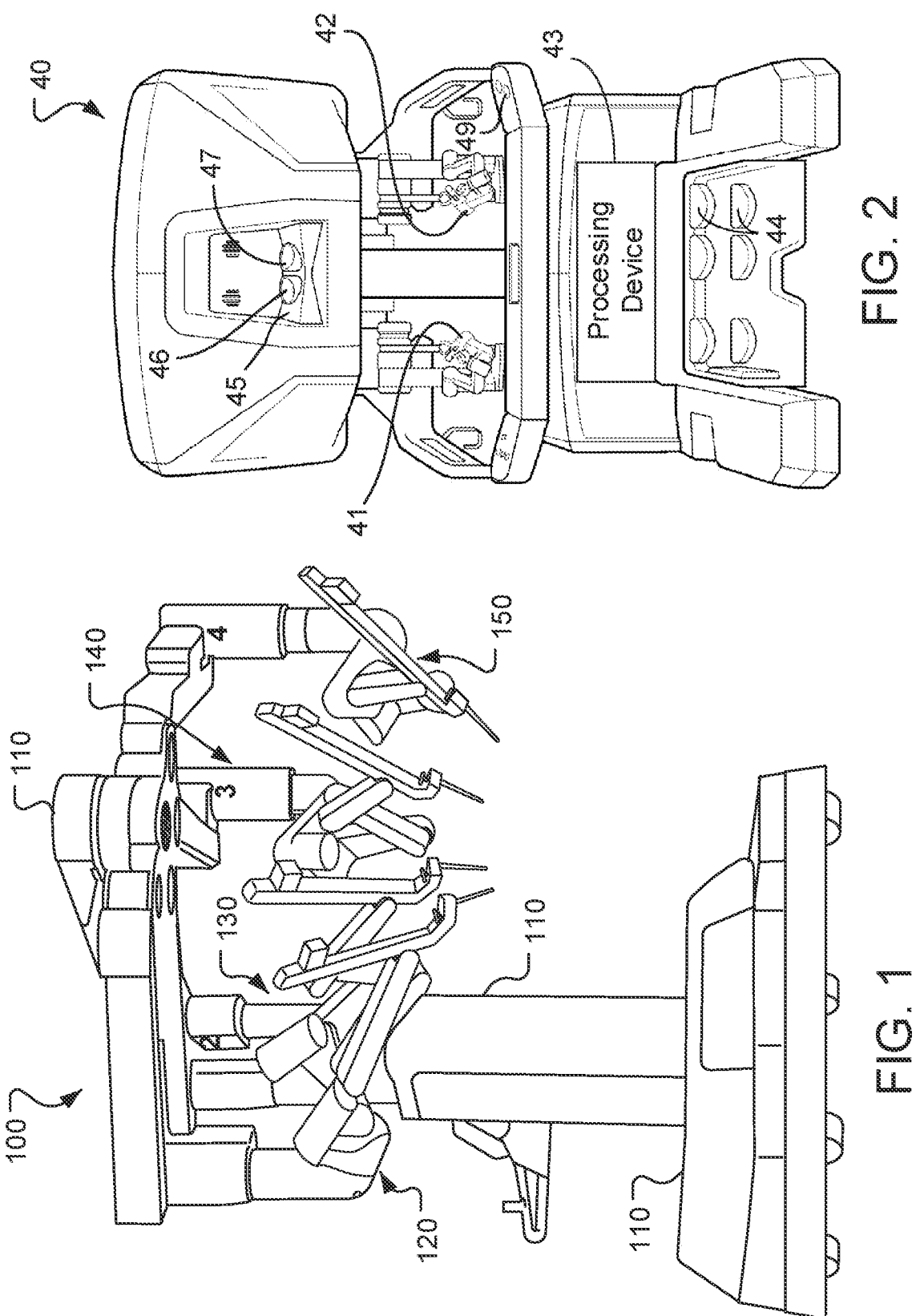
FIG. 1 is a perspective view of an example patient-side cart of a computer-assisted tele-operated surgery system.
FIG. 2 is a front view of an example surgeon console of a computer-assisted tele-operated surgery system.

Referring to FIGS. 1 and 2, systems for minimally invasive computer-assisted tele-surgery (also referred to as MIS) can include a patient-side cart 100 and a surgeon console 40. Tele-surgery is a general term for surgical systems where the surgeon uses some form of remote control, e.g., a servo-mechanism, or the like, to manipulate surgical instrument movements rather than directly holding and moving the instruments by hand. The robotically manipulatable surgical instruments can be inserted through small, minimally invasive surgical apertures to treat tissues at surgical sites within the patient, avoiding the trauma associated with accessing for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

In the depicted embodiment, the patient-side cart 100 includes a base 110, a first robotic manipulator arm assembly 120, a second robotic manipulator arm assembly 130, a third robotic manipulator arm assembly 140, and a fourth robotic manipulator arm assembly 150. Each robotic manipulator arm assembly 120, 130, 140, and 150 is pivotably coupled to the base 110. In some embodiments, fewer than four or more than four robotic manipulator arm assemblies may be included as part of the patient-side cart 100. While in the depicted embodiment the base 110 includes casters to allow ease of mobility, in some embodiments the patient-side cart 100 is fixedly mounted to a floor, ceiling, operating table, structural framework, or the like.

In a typical application, two of the robotic manipulator arm assemblies 120, 130, 140, or 150 hold surgical instruments and a third holds a stereo endoscope. The remaining robotic manipulator arm assembly is available so that another instrument may be introduced at the work site. Alternatively, the remaining robotic manipulator arm assembly may be used for introducing a second endoscope or another image capturing device, such as an ultrasound transducer, to the work site.

Each of the robotic manipulator arm assemblies 120, 130, 140, and 150 is conventionally formed of links that are coupled together and manipulated through actuatable joints. Each of the robotic manipulator arm assemblies 120, 130, 140, and 150 includes a setup arm and a device manipulator. The setup arm positions its held device so that a pivot point occurs at its entry aperture into the patient. The device manipulator may then manipulate its held device so that it may be pivoted about the pivot point, inserted into and retracted out of the entry aperture, and rotated about its shaft axis.

In the depicted embodiment, the surgeon console 40 includes a stereo vision display 45 so that the user may view the surgical work site in stereo vision from images captured by the stereoscopic camera of the patient-side cart 100. Left and right eyepieces, 46 and 47, are provided in the stereo vision display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices, which in turn control the motion of robotic instruments.

The surgeon console 40 also includes left and right input devices 41, 42 that the user may grasp respectively with his/her left and right hands to manipulate devices (e.g., surgical instruments) being held by the robotic manipulator arm assemblies 120, 130, 140, and 150 of the patient-side cart 100 in preferably six degrees-of-freedom ("DOF"). Foot pedals 44 with toe and heel controls are provided on the surgeon console 40 so the user may control movement and/or actuation of devices associated with the foot pedals.

A processing device 43 is provided in the surgeon console 40 for control and other purposes. The processing device 43 performs various functions in the medical robotic system. One function performed by processing device 43 is to translate and transfer the mechanical motion of input devices 41, 42 to actuate their respective joints in their associated robotic manipulator arm assemblies 120, 130, 140, and 150 so that the surgeon can effectively manipulate devices, such as the surgical instruments. Another function of the processing device 43 is to implement the methods, cross-coupling control logic, and controllers described herein.

The processing device 43 can include one or more processors, digital signal processors (DSPs), and/or microcontrollers, and may be implemented as a combination of hardware, software and/or firmware. Also, its functions as described herein may be performed by one unit or divided up among a number of subunits, each of which may be implemented in turn by any combination of hardware, software and firmware. Further, although being shown as part of or being physically adjacent to the surgeon console 40, the processing device 43 may also be distributed as subunits throughout the tele-surgery system. One or more of the subunits may be physically remote (e.g., located on a remote server) to the tele-surgery system.

Figure 3:
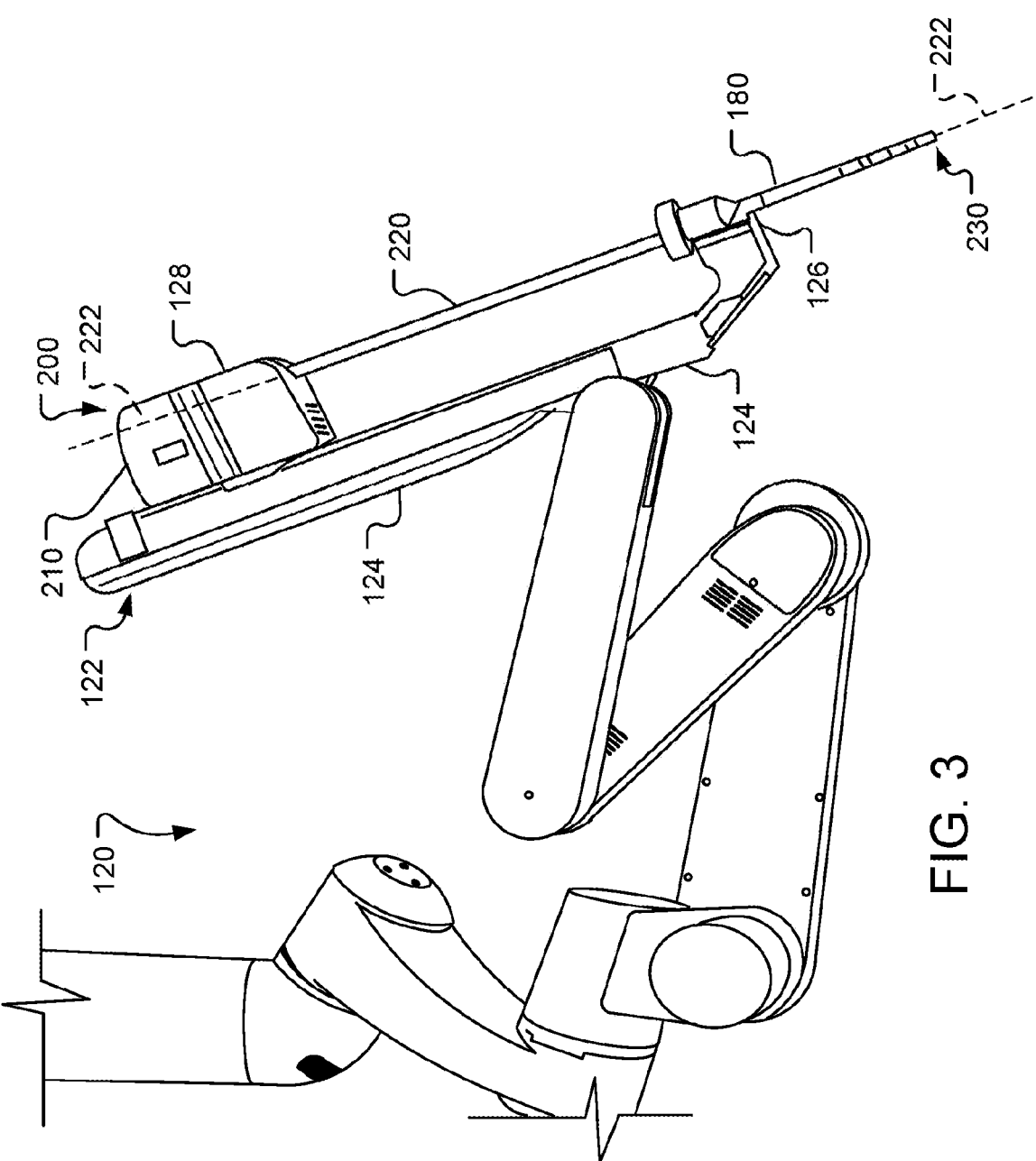
FIG. 3 is a side view of an example robotic manipulator arm assembly of a computer-assisted tele-operated surgery system.

Referring also to FIG. 3, the robotic manipulator arm assemblies 120, 130, 140, and 150 can manipulate devices such as surgical instruments to perform MIS. For example, in the depicted arrangement the robotic manipulator arm assembly 120 is pivotably coupled to an instrument holder 122. A cannula 180 and a surgical instrument 200 and are, in turn, releasably coupled to the instrument holder 122. The cannula 180 is a tubular member that is located at the patient interface site during a surgery. The cannula 180 defines a lumen in which an elongate shaft 220 of the surgical instrument 200 is slidably disposed. As described further below, in some embodiments the cannula 180 includes a distal end portion with a body wall retractor member. The instrument holder 122 is pivotably coupled to a distal end of the robotic manipulator arm assembly 120. In some embodiments, the pivotable coupling between the instrument holder 122 and the distal end of robotic manipulator arm assembly 120 is a motorized joint that is actuatable from the surgeon console 40 and processor 43.

The instrument holder 122 includes an instrument holder frame 124, a cannula clamp 126, and an instrument holder carriage 128. In the depicted embodiment, the cannula clamp 126 is fixed to a distal end of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some embodiments, the movement of the instrument holder carriage 128 along the instrument holder frame 124 is a motorized, translational movement that is actuatable/controllable by the processor 43. The surgical instrument 200 includes a transmission assembly 210, the elongate shaft 220, and an end effector 230. The transmission assembly 210 may be releasably coupled with the instrument holder carriage 128. The shaft 220 extends distally from the transmission assembly 210. The end effector 230 is disposed at a distal end of the shaft 220.

The shaft 220 defines a longitudinal axis 222 that is coincident with a longitudinal axis of the cannula 180. As the instrument holder carriage 128 translates along the instrument holder frame 124, the elongate shaft 220 of the surgical instrument 200 is moved along the longitudinal axis 222. In such a manner, the end effector 230 can be inserted and/or retracted from a surgical workspace within the body of a patient.

Figure 4A:
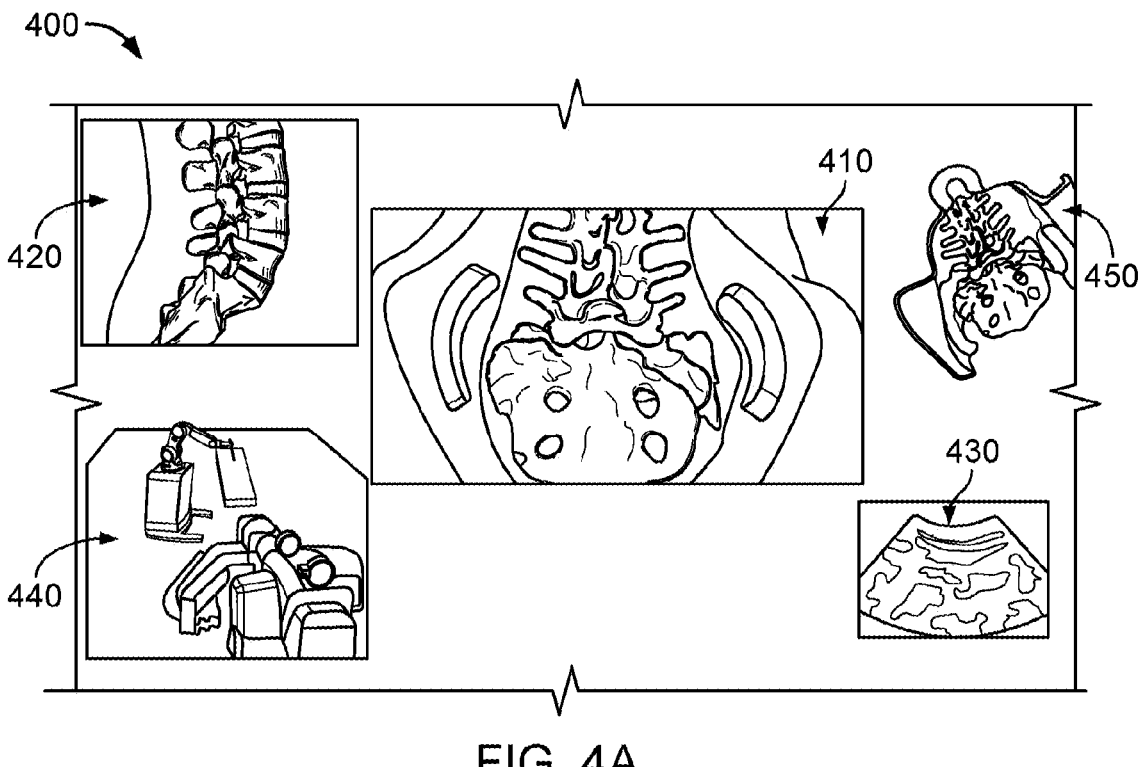
FIGS. 4A and 4B are example configurations of a display associated with a computer-assisted tele-operated surgery system.
Figure 4B:
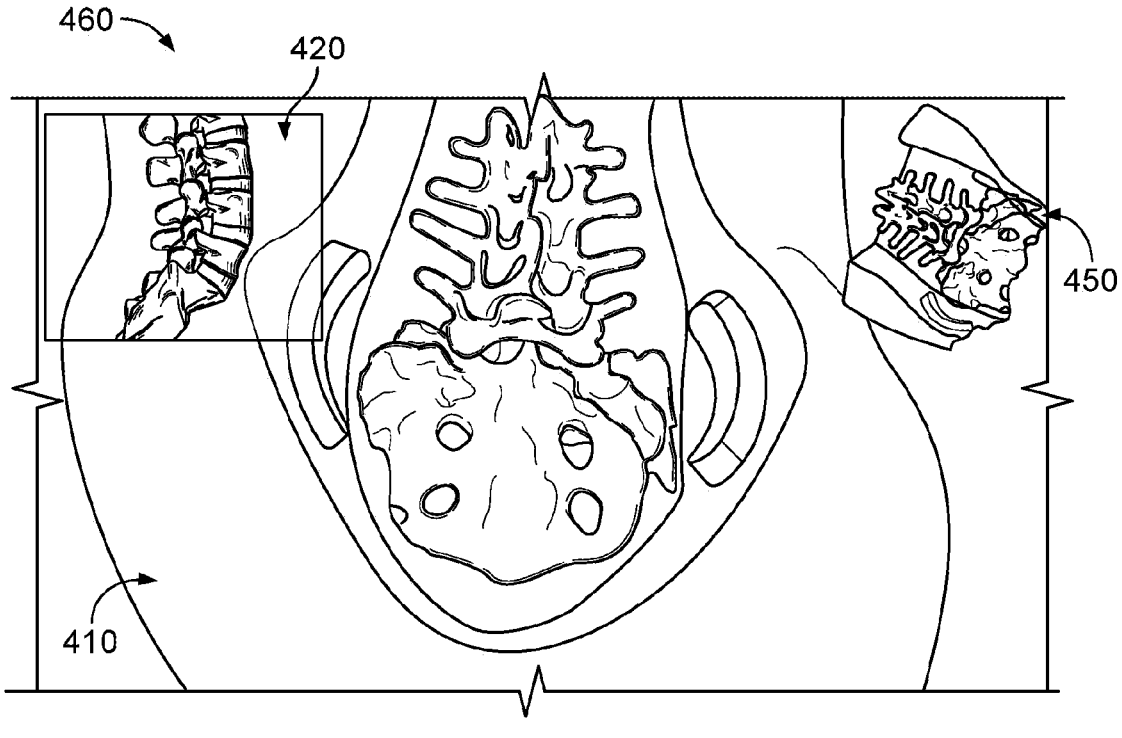

FIGS. 4A and 4B are example configurations of a display associated with a computer-assisted tele-operated surgery system. For example, the configurations shown in the examples of FIGS. 4A and 4B may be visible in the stereo vision display 45 described above with reference to FIG. 2. In some implementations, the display configuration 400 can include visual representations of data from multiple data sources. For example, the example configuration 400 includes an endoscope video feed (or image) 410, an X-Ray image 420, an ultrasound image 430, a representation 440 of surgical tools (e.g., real tools or virtual proctoring tools), and a three-dimensional (3D) visualization 450. Visual representations from other sources may also be displayed. For example, the sources can include an endoscope (providing images/video feed in the visual, near infra-red (NIR) or other parts of the spectrum), an ultrasound imaging device (2D or 3D), a computed tomography (CT) imaging device, a nuclear imaging device, a radiography imaging device, and a magnetic resonance imaging (MRI) device, and an X-Ray fluoroscope device. In some implementations, the source is a storage device storing pre-recorded video or images. In such cases stored images, data, or videos associated with a surgical process may also be displayed in accordance with user-preferences. For example, the display device may be connected to a laptop, smartphone, tablet, or other computing device to display pre-operative or inter-operative scans, test results, notes or other image or text-based information. In some implementations, a source can include a processing device generating a graphical user interface (GUI) that includes one or more controls, for example, for adjusting or configuring the display device.

Figure 4C:
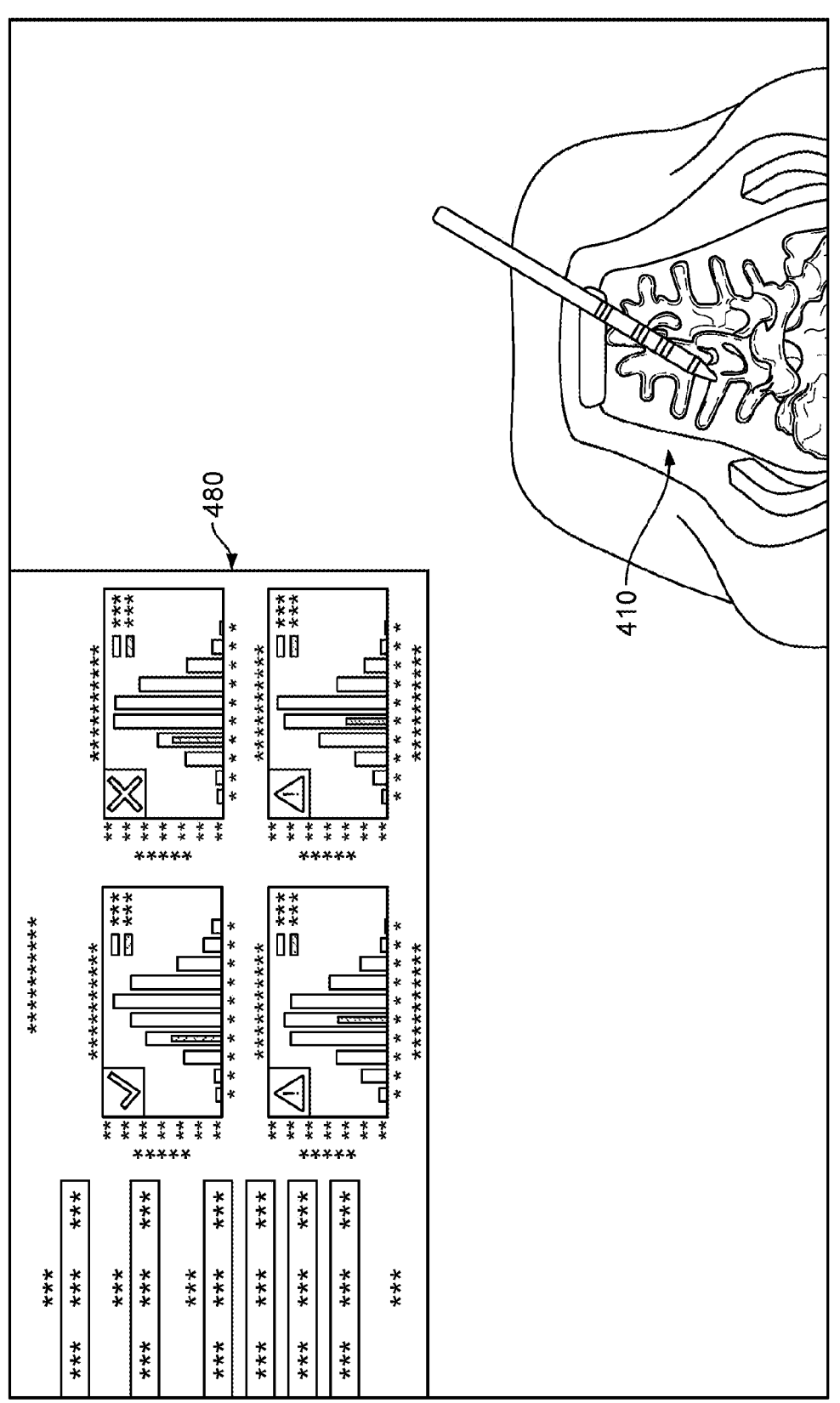
FIG. 4C is an example illustrating display of data overlaid on an endoscope image.

The images or video feeds from the multiple sources may be configured in various ways. In some implementations, the visual representations from the multiple sources may be arranged within the available real-estate of the display device at substantially non-overlapping portions as per corresponding user-preferences. An example of such a configuration is shown in FIG. 4A. In some implementations, the visual representations corresponding to one or more sources may be removed from (or minimized) and/or added to the visible area of the display device. In some implementations, one or more visual representations may be displayed as an overlay on another image. This is shown as an example in the configuration 460 of FIG. 4B, where the endoscope image 410 is displayed as the main image, and the X-ray image 420 and the 3D visualization 450 are displayed as overlays on the endoscope image 410. Another example is shown in FIG. 4C, where a visual representation 480 including text and image based information is displayed as an overlay on the endoscope image 410.

In some implementations, where an image is displayed as an overlay on another image, the two images may be registered with respect to one another. For example, if the images being displayed are geo-tagged with location information (e.g., position and orientation with respect to the origin of a known coordinate system), they may be aligned with respect to one another based on the location information associated with the individual images. The alignment can be calculated, for example, via an image registration process that includes transforming the sets of data corresponding to the acquired images into one coordinate system based on location information corresponding to the images. This can also be referred to as warping, and can include various rigid or non-rigid transformations such as translation, rotation, shear etc.

Figure 5A:
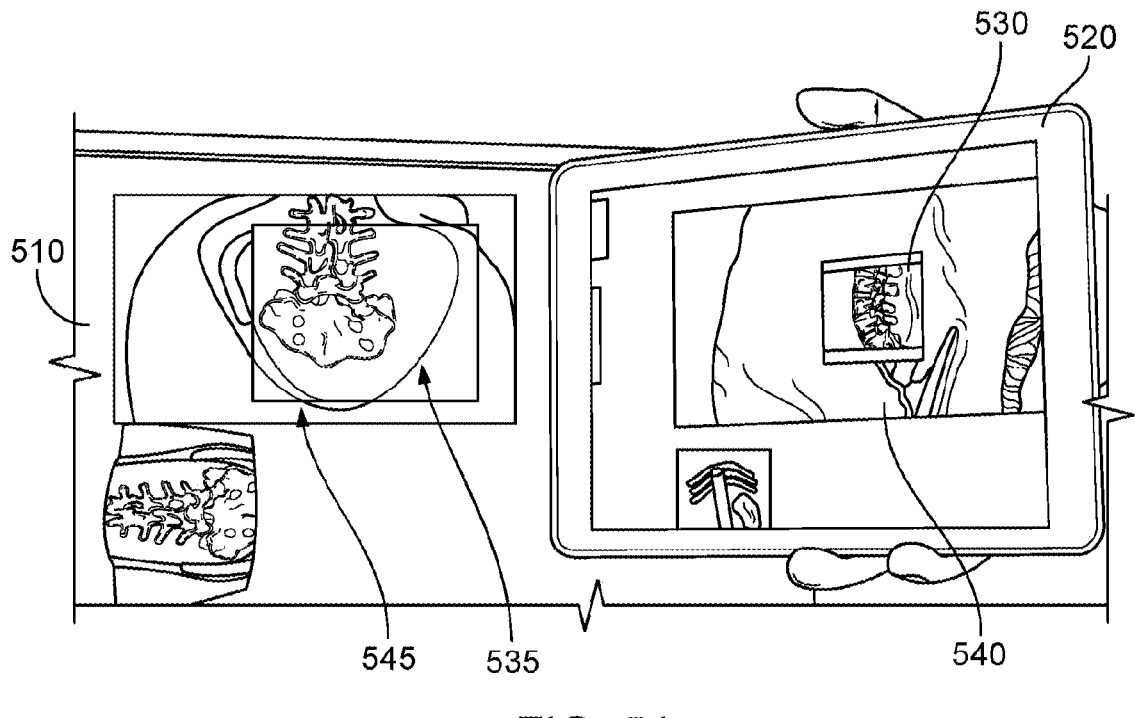
FIGS. 5A and 5B show examples of how a display associated with a computer-assisted tele-operated surgery system may be configured by a user.
Figure 5B:
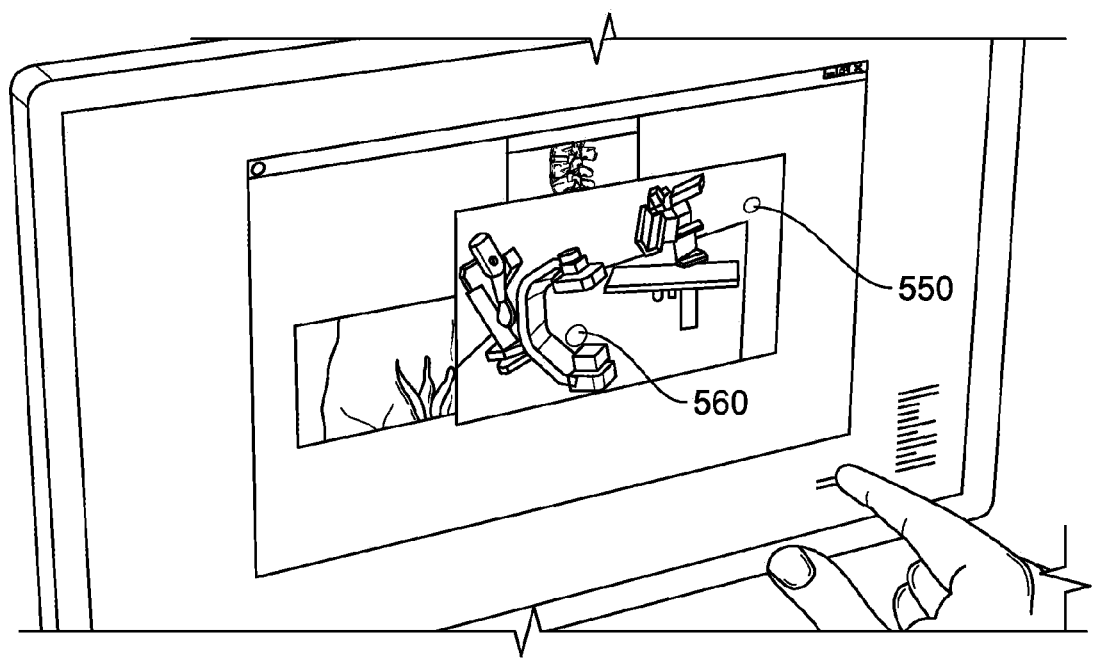

The configuration of the visual representations from the multiple sources can be done in various ways. Examples of how a display associated with a computer-assisted tele-operated surgery system may be configured are shown in FIGS. 5A and 5B. In some implementations, and as shown in FIG. 5A, the configuration may be done using a touch-based interface. In such cases, a touchscreen device 520 (e.g., a tablet computer) can be provided to the user to perform touch based adjustments of the visual representations. The adjustments can be configured to be reflected on a second display device 510 such as the display device 45 associated with the surgeon's console 40 described above with reference to FIG. 1. For example, moving an ultrasound image 530 over an endoscope image 540 on the touchscreen device 530 can cause a corresponding ultrasound image 535 to move over a corresponding endoscope image 545 on the second display device 510. Examples of configuration operations that may be possible using a touch-based user interface include moving visual representations to different portions of the screen, controlling 3D poses of displayed objects, rotating a rendered volumetric image, and performing adjustments for registering two images.

In some implementations, the user-interface can be touchless. An example of such an interface is shown in FIG. 5B. In such cases, the visual representations may be configured, for example, using gestures but without touching the display device. In the example shown in FIG. 5B, the index finger and the thumb of the user are detected and displayed on the display device as the points 550 and 560, respectively. Moving the index finger and thumb causes the points 550 and 560 to move on the display device, thereby allowing the underlying visual representations to be adjusted, for example, as if the user is touching the display device at the points 550 and 560.

Other forms of user interfaces may also be used. In some implementations, other touchless technologies such as gaze tracking may be used to configure the visual representations on a display device. In some implementations, input device(s) for the physical operation of the surgical system (such as master tool manipulators (MTM) available on da Vinci® Surgical Systems, wireless input devices, or gesture detection systems, among others) may be used for configuring the visual representations. In some implementations, dedicated configuration control input systems (such as a keypad, touchpad, touchscreen, or joystick, among others) may be used for configuring the visual representations (and optionally any other aspects to the surgical system not involving physical operation of the system).

Figure 6:
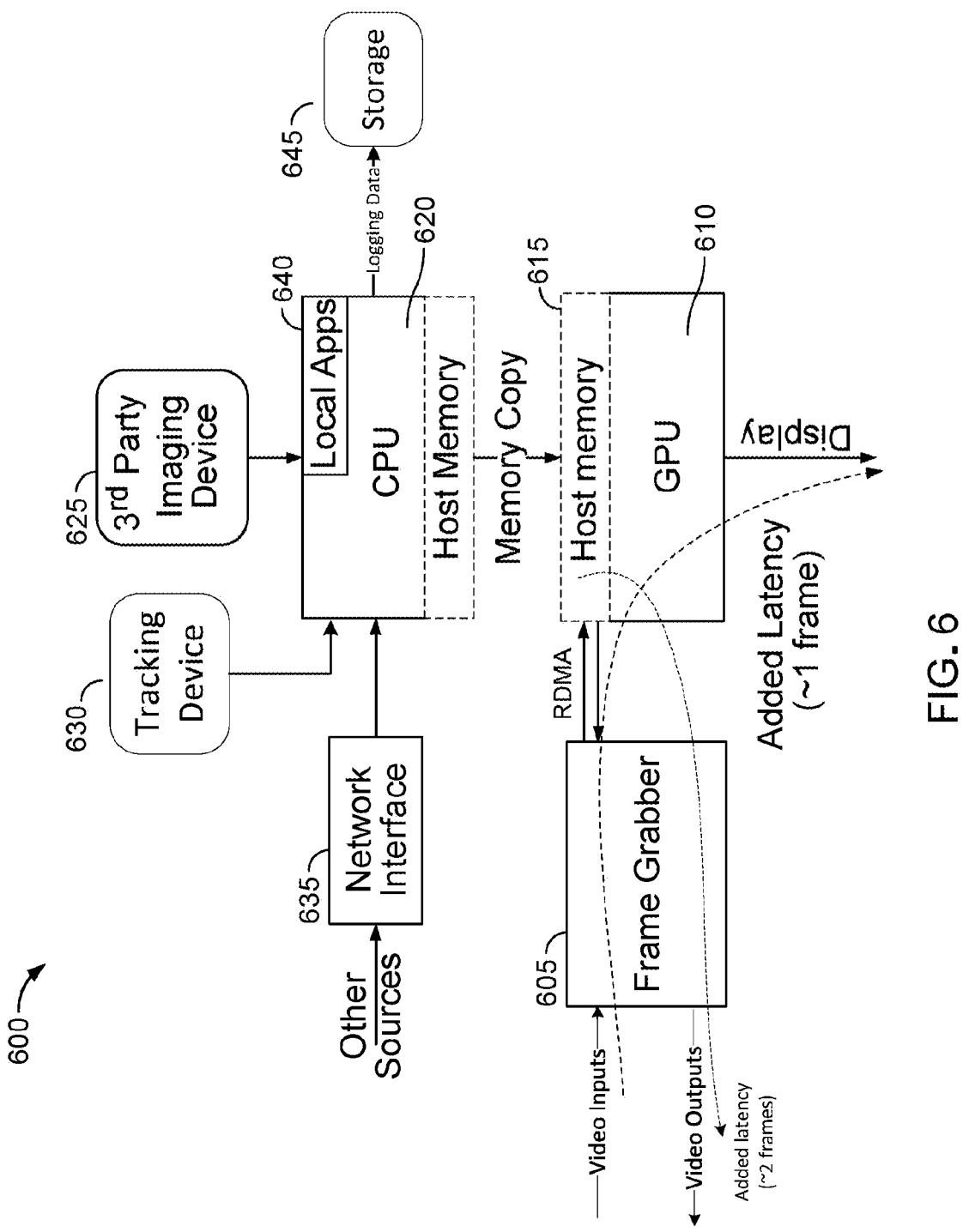
FIG. 6 is an example block diagram of a system for displaying images from multiple data sources.

FIG. 6 is an example block diagram of a system 600 for displaying images from multiple sources. In some implementations, the system 600 may help in maintaining display latency to below threshold levels associated with computer-assisted tele-operated surgery systems. For example, certain operating guidelines may specify that the maximum tolerable perceived latency for a tele-operated system is less than 100 milliseconds. This can be the case, for example, in da Vinci® Surgical Systems where endoscopic images may be used for closing a master-slave control loop, thereby affecting the transparency of master-slave control. In such cases the perceived latency can be the sum of (i) a latency from when an action happens until a representation of the action is displayed on the da Vinci® surgeon console and (ii) the latency from when the user moves master manipulators until the slave instruments make the corresponding motion. In some implementations, the system 600 can include a frame grabber unit 605 that digitizes incoming video frames and transfers the digitized images to a graphics processing unit (GPU) 610 via remote direct memory access (RDMA) to the GPU memory 615. The incoming video frames can be sent to the display device from the GPU 610, thereby avoiding the central processing unit (CPU) 620 in the processing path of the images. This in turn may keep the latency associated with the endoscopic images below a tolerable threshold. In some implementations, data from one or more other sources (e.g., a third party imaging device 625 or a tracking device 630) may traverse through both the CPU 620 and the GPU 610 before being displayed on the display device. The system 600 may also include a network interface card 635 for routing data from one or more sources to the CPU 620. In some implementations, the composed images may be routed back to the frame grabber 605 via ROMA transfer and the video output may be provided via the frame grabber. In some implementation, the video inputs and video outputs to/from the frame grabber 605 may be routed via a high bandwidth fiber optic link. In some implementations, the CPU 620 may execute one or more applications 640 for processing the data received from the one or more sources. One application may be logging of data, including video data from multiple sources to a local storage 645.

In some implementations, one or more video sources connected to the CPU 620 may each be identified using a unique identifier and/or a set of parameters (e.g., image size, color or grayscale, mono or stereo, frame rate, etc.). The source may be a video stream or an image that occasionally gets updated. The source may also be linked to a particular position on the display device, for example, based on user preferences or user-inputs. In some implementations, the display area on which the visual representation from a particular source may be positioned is larger than the physical visible area of the display device. In such cases, portions of the display area may be moved in or out of the physical display area based on user input. In some implementations, where an image from a particular source is registered with respect to another image, the particular source may be linked, for example, with a transformation matrix with respect to a common coordinate system or with respect to the other image's transformation. The parameters and identifiers associated with each source may be stored as a module, and modules may be added removed or modified in run time to configure visual representations from corresponding sources. A module corresponding to a source may be modified at run time, for example, at a real-time or near real-time basis. For example, non-image information (e.g., text, charts etc.) may be added to a module associated with a source for the non-image information to be displayed together with a visual representation of the corresponding source. In some cases, by making the latency associated with a particular source (e.g., endoscopic images) independent of the other image sources, the system 800 described with reference to FIG. 8 may provide a flexible framework for implementing a reconfigurable display system for a computer-assisted tele-operated surgery system.

The visual representations of signals from the multiple sources may be configured in various ways. In some implementations, a surgeon may configure the visual representations on the display device (using user interfaces and/or input devices described above) and store the preferences within a user-profile. The user-profile may then be saved at a storage location (e.g., a remote server or local storage device) and downloaded by others as needed. For example, a senior surgeon may save his/her preferences in such a user-profile for junior/trainee surgeons to user or review. In some implementations, the preferences stored within a user-profile may reflect preferences of an institution (e.g., a hospital) or regulations promulgated by a regulatory body.

In some implementations, the configuration can be specific to various phases of a surgery. For example, during an initial phase of a surgery (e.g., when a surgeon is making an incision) a surgeon may prefer to have the entire display area to be occupied by the endoscope image. However, during a later phase (e.g., when arteries are being clamped), the surgeon may prefer to see corresponding CT images showing the vasculature, either as an independent image, or registered over the endoscopic image. The phase-dependent configurations may be stored on a storage device and loaded as needed upon determination of a particular phase of the surgical process. The determination that signals being received from one or more sources correspond to a particular phase of the surgery may be done in various ways. In some implementations, the determination may be made based on manual user-input (e.g., voice-input or user-input received through an input device). For example, a surgeon may provide user-input indicative of a new phase in the surgery, and the corresponding phase-dependent display profile may be loaded accordingly. In some implementations, the phase determination may be made automatically, for example, by processing one or more images from a source. For example, the endoscope image/feed may be analyzed to detect the presence of a particular anatomical feature or surgical tool, and the phase of the surgery may be determined accordingly. If an endoscope image is analyzed to detect the presence of a clamp, a determination may be made that the surgeon intends to clamp a portion of the vasculature, and accordingly, a CT image that highlights the vasculature may be displayed. As such, the contents of a visual representation corresponding to one or more sources may be analyzed in various ways to make such determinations. In some implementations, the events generated by the surgical system (e.g., da Vinci® surgical system) may be used to determine the phase of surgery or be used as indications for change in the display layout. In some implementations, artificial intelligence processes (e.g., machine learning based processes) may be used in determining phases of a surgical process. In some cases, such dynamic phase-based reconfiguration may help in improving a surgeon's user-experience, for example, by loading an appropriate display configuration automatically.

In some implementations, the configurability of the display device may be delimited, for example, based on one or more safety conditions. In such cases, if a surgeon attempts to configure the visual representations from the sources in a way that violates a safety condition, the system may prevent such a configuration and/or generate one or more alerts to flag the violation. For example, in certain surgical processes, a safety condition may require that the endoscope feed is always displayed on the display device. In such cases, if a surgeon attempts to remove the endoscope feed from the display device (or reduce it to a size smaller than an allowable threshold), the system may prevent the surgeon from making such an adjustment, and/or generate an alert (e.g., a visual or audible alarm) indicating that the safety condition has been violated. Other safety conditions may cause one or more visual representations to be "locked" within the display device such that a user may not remove (or possibly even resize) such visual representations. In some implementations, a supervisor process may monitor the configuration of the display device, and take one or more actions if a safety condition is violated. For example, if a safety condition is violated, control of the surgical tools and/or robotic arms may be affected to alert the surgeon of the violation. For example, if a determination is made that the surgeon is not looking at the endoscope feed (e.g., using gaze tracking), the system may limit sensitivity of one or more instruments to reduce the chances of accidental injuries to unintended portions. In some cases, such generation of control signals based on determining a violation of a safety condition may improve the safety of surgical processes performed using computer-assisted tele-operated surgical systems.

In some implementations, one or more image sources or other sources of information may be processed to detect the occurrence of one or more events, and take one or more actions based on associated rules. For example, if processing of endoscope images reveals the occurrence of bleeding, and the user display configuration in the meantime has a preoperative image covering most of the display, the system may be configured to automatically change the display configuration to bring the endoscope images to the surgeon's attention, possibly in conjunction with one or more visual or audio warnings. Rules for such safety measures can be set based on predetermined safety logic. The rules can also be implemented via machine learning tools such as neural networks trained on pre-collected and annotated datasets.

In some implementations, one or more image sources may be processed in the background to detect certain events that may trigger changes in the display mode, for example, to present more information to the surgeon when required. Fluorescence imaging is often used to investigate tissue perfusion or to view lymph nodes during surgery. For fluorescence imaging, fluorescent compounds can be injected locally or via vasculature and an endoscope camera can be operated in an appropriate mode to capture fluorescence. In some implementations, the user may continue working with normal endoscope images, while a background process analyzes the observed fluorescence. In some implementations, the display can be configured to automatically switch to showing the fluorescence images (or a composed white-light fluorescence endoscope image) upon detecting that an amount of the fluorescence exceeds a threshold.

In some implementations, one or more processes or filters may be applied to an image source based on detection of the phase of surgery. For example, the system can be configured to detect that an instrument is being used to burn and cut soft tissue, and accordingly, a haze removal process can be automatically applied to the processing pipeline for the endoscope images. As another example, when an energy instrument (e.g., an instrument used for burning or cutting soft tissue) is used, the ultrasound image display can be automatically hidden (or at least reduced in size), for example, to make sure that the user has an adequately large view of the endoscopic images. In some implementations, if the ultrasound images are affected by the noise from the energy instruments, such images may also be prevented from being displayed.

Figure 7:
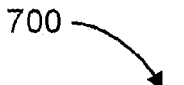
FIG. 7 is a flowchart illustrating an example process of providing feedback to a healthcare professional during a surgical process.
Figure 7:
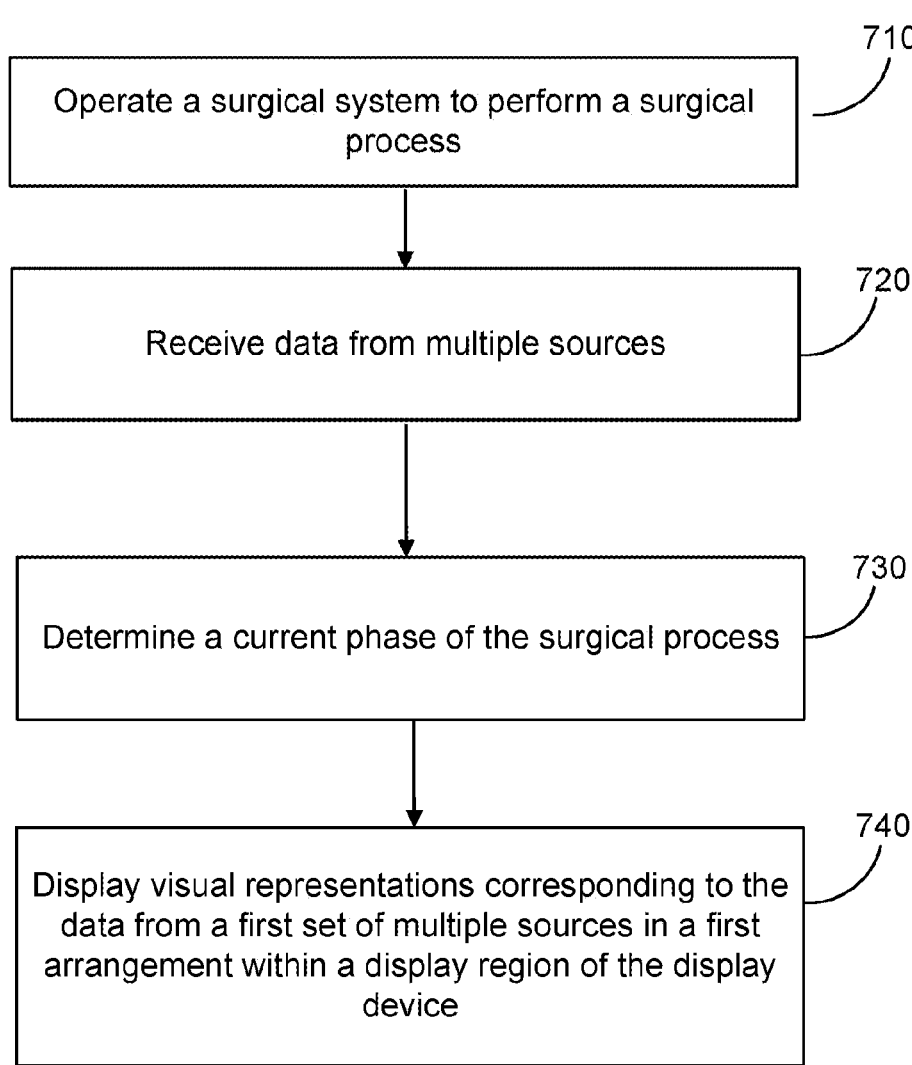

FIG. 7 is a flowchart illustrating an example process 700 of displaying visual representations of data during a surgical process. In some implementations, at least a portion of the process 700 may be executed at a surgeon's console of a computer-assisted tele-operated surgery system (e.g., by the processing device 43 of the surgeon's console 40 depicted in FIG. 2). Operations of the process 700 include operating a surgical system to perform a surgical process (710). This can include, for example, receiving one or more commands at the processing device 43 via input devices of the surgeon's console 40, and generating control signals for operating the patient-side cart 100. Operations of the process 700 also include receiving data from multiple data sources (720). The multiple data sources can include, for example, at least two of: an endoscope, an ultrasound imaging device, a computed tomography (CT) imaging device, a nuclear imaging device, a radiography imaging device, and a magnetic resonance imaging (MRI) device. In some implementations, the multiple data sources can include a computing device generating one or more of an image, text, interactive graphics, or a graphical user interface (GUI). The multiple data sources can also include a storage device providing one or more pre-stored images or videos. In some implementations, one or more of the signals from the multiple data sources may include location information (e.g., based on data from position sensors such as EM, optical, RF, or shape sensors, kinematic modeling, image recognition/tracking, or any other modality) with respect to a coordinate system.

Operations of the process 700 also includes determining a current phase of the surgical process (730). This may be done in various ways. In some implementations, determining the current phase may be based on a user-input (e.g., voice input, or input provided through an input device) indicative of the current phase. In some implementations, the determination can be made automatically, for example, based on an image analysis process executed on signals from at least one of the multiple sources.

Operations of the process 700 further includes displaying, on the display device, visual representations corresponding to the data from a first set of the multiple sources in a first arrangement within a display region of the display device (740). At least one of the first set of the multiple sources and the first arrangement is associated with the current phase of the surgical process. In some implementations, upon determination of a new phase of the surgical process, at least one of the first set of the multiple sources or the first arrangement is updated. The updating can be based on, for example, based on a user preference record for a current user of the surgical system. Such user preference records may be maintained, for example, as a user profile. In some implementations, the updating can be based on a predetermined safety profile for the surgical system.

The first arrangement can be determined, for example, based on a user profile. In some implementations, the user-profile may be loaded prior to the commencement of the surgical process. In some implementations, the user profile can identify an individual performing the surgical process, and include the user-preferences of the individual regarding organization of the visual representations of the signals from the multiple sources during different phases of the surgical process. In some implementations, if the user adjusts one or more visual representations, the user profile may be updated in accordance with such adjustments. In some implementations, a representation of a user-profile may be stored at a storage location accessible to other users.

In some implementations, user-input indicative of adjustments to one or more of the visual representations may be received via an input device, and the display device may be updated in accordance with the adjustments. In some implementations, data from the one or more multiple data sources can include position data with respect to a common frame of reference (e.g., a common coordinate system). In such cases, displaying the visual representations can include overlaying a first visual representation on a second visual representation in accordance with that common reference frame. In some implementations, the display device can include multiple screens or display areas (e.g., a main display that shows active visual representations, and a side display that shows the visual displays that are minimized or not being used). In some implementations, the display area may be larger than the physical dimensions of the viewable area of the display device, and portions of the display area may be dragged in and out of the viewable area as needed. In some implementations, when two visual representations from two sources are associated with a common frame of reference, dragging one of those visual representations onto the other can cause it to "snap" into registration with the other, thereby ensuring that the visual representations are properly aligned.

Figure 8:
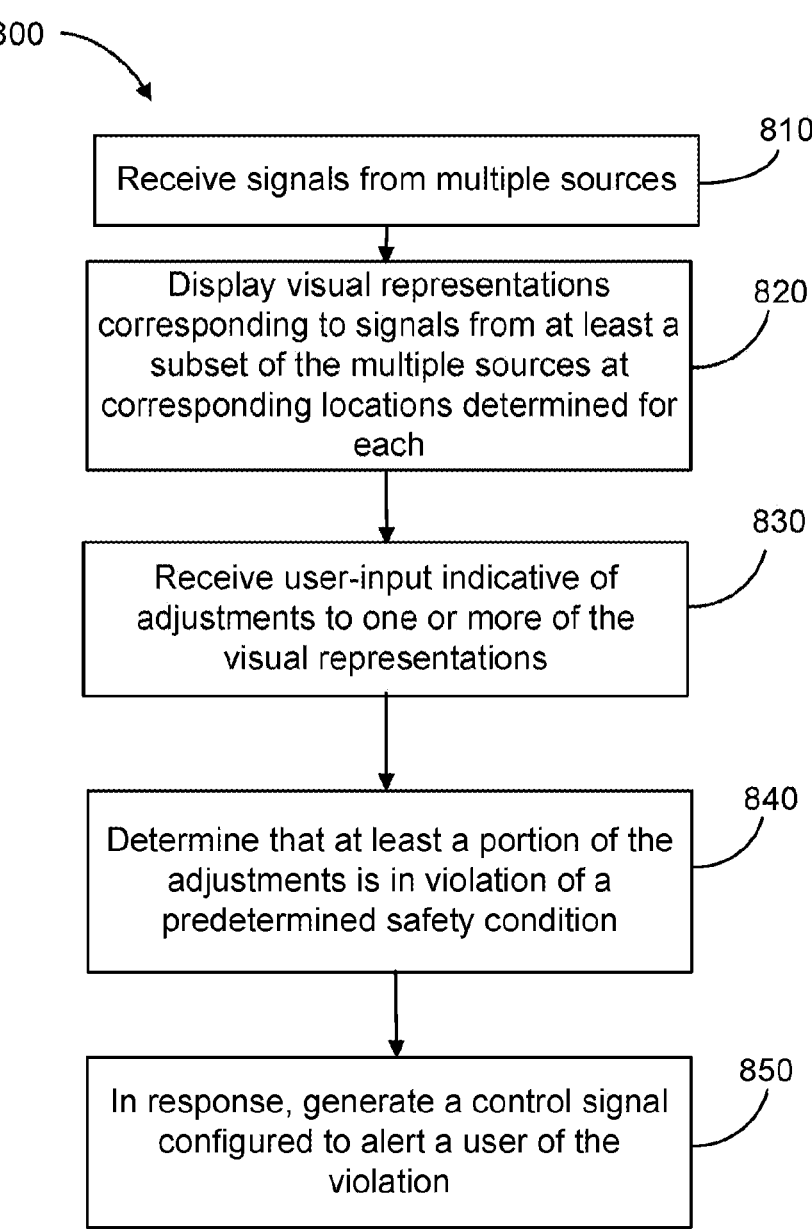
FIG. 8 is a flowchart illustrating an example process of controlling configurability of visual representations from multiple data sources.

FIG. 8 is a flowchart illustrating an example process 800 of controlling configurability of visual representations from multiple sources. In some implementations, at least a portion of the process 800 may be executed at a surgeon's console of a computer-assisted tele-operated surgery system (e.g., by the processing device 43 of the surgeon's console 40 depicted in FIG. 2). Operations of the process 800 includes receiving signals from multiple sources (810). The multiple sources can include the sources as described above with reference to FIG. 8. The operations of the process 800 also includes displaying visual representations corresponding to the signals from at least a subset of the multiple sources at locations determined for each of the visual representations (820). In some implementations, the subset of the multiple sources and/or the corresponding locations may be determined based on user preferences stored within a user-profile.

Operations of the process 800 further includes receiving user-input indicative of adjustments to one or more of the visual representations (830). A surgeon may need to readjust the default positions and/or size of the visual representations in accordance with the particular surgery at hand, and may make such adjustments using an input device or user interface described above. For example, a surgeon performing a nephrectomy may prefer to have ultrasound images aligned or registered to the endoscope feed, and have the CT images on one side for reviewing as needed. Accordingly, the surgeon may make the necessary adjustments to an existing display configuration, for example, using an input device such as a tablet computer (e.g., as shown in FIG. 5A), a touchless input device (e.g., as shown in FIG. 5B), a haptic device, or a gaze-tracking based input device.

Operations of the process 800 further includes determining that at least a portion of the adjustments is in violation of a predetermined safety condition associated with the corresponding visual representation (840). For example, a safety condition associated with an endoscope feed may specify that the visual representation of the feed may not be reduced to a size smaller than a threshold. In such a case, if a user attempts to reduce the visual representation of the endoscope feed to a size smaller than the threshold, a violation of the safety condition may be determined. In another example, determining the violation can include detecting that the user-input is requesting a particular visual representation to be removed from the display device, whereas the corresponding predetermined safety condition specifies that the particular visual representation to be displayed throughout the surgical process. In some implementations, determining the violation can also include detecting (e.g., via gaze tracking) that a user is looking at an incorrect visual representation during the adjustment process.

Operations of the process 800 also includes generating, responsive to determining the violation, a control signal configured to alert a user of the violation (850). In some implementations, the control signal can be configured to disable (or reduce the sensitivity of) one or more instruments being used in the surgical process. The control signal may also cause the generation of a visible or audible message that alerts the user of the violation. In some implementations, the control signal may cause the violating adjustment to be undone or reversed, and alert the user that such a readjustment has been made. The predetermined safety conditions can be specific to the various visual representations, and/or specific to particular phase of the surgical process.

The functionality described herein, or portions thereof, and its various modifications (hereinafter "the functions") can be implemented, at least in part, via a computer program product, e.g., a computer program tangibly embodied in an information carrier, such as one or more non-transitory machine-readable media or storage device, for execution by, or to control the operation of, one or more data processing apparatus, e.g., a programmable processor, a DSP, a micro-controller, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed one or more processing devices at one site or distributed across multiple sites and interconnected by a network.

Actions associated with implementing all or part of the functions can be performed by one or more programmable processors or processing devices executing one or more computer programs to perform the functions of the processes described herein. All or part of the functions can be implemented as, special purpose logic circuitry, e.g., an FPGA and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method comprising:
   operating a surgical system to perform a surgical process, the surgical system comprising a display device, and the surgical process comprising a plurality of phases;
   determining that a current phase of the surgical process corresponds to a first phase of the plurality of phases;
   generating, based on at least a profile and determining that the current phase corresponds to the first phase, a first display configuration for first visual representations corresponding to data from a first set of data sources selected from multiple data sources, the profile defining a configuration for visual representations presentable on the display device, wherein the configuration for the visual representations limits certain adjustments to a size of a view or prevents the view from being removed from the display device by a user, the configuration further defining a minimum size of the view presentable on the display device, the minimum size being defined by a safety condition specific to the current phase of the surgical process; and
   presenting, on the display device, the first display configuration for the first visual representations.

2. The method of claim 1, further comprising:
   determining that the current phase of the surgical process corresponds to a second phase of the plurality of phases;
   generating, based on at least the profile and determining that the current phase corresponds to the second phase, a second display configuration for second visual representations corresponding to data from a second set of data sources selected from the multiple data sources; and
   presenting, on the display device, the second display configuration for the second visual representations.

3. The method of claim 1, further comprising, after presenting the first display configuration for the first visual representations:
   receiving a user input indicative of an adjustment to the first display configuration for the first visual representations;
   determining whether the adjustment violates a safety condition associated with the profile; and
   presenting, on the display device:
       an updated display configuration of the visual representations based on at least the user input if the adjustment is determined to violate the safety condition; or
       the first display configuration if the adjustment is determined to not violate the safety condition.

4. The method of claim 3, wherein:
   determining whether the adjustment violates the safety condition associated with the profile comprises:
       determining that the adjustment violates the safety condition; and
   the method further comprises:
       presenting, on the display device, an alert indicating that the adjustment violates the safety condition.

5. The method of claim 1, wherein:
   the multiple data sources comprise at least two of: an endoscope, an ultrasound imaging device, a computed tomography (CT) imaging device, a nuclear imaging device, a radiography imaging device, or a magnetic resonance imaging (MRI) device.

6. The method of claim 1, wherein:
   determining that the current phase of the surgical process corresponds to the first phase of the plurality of phases comprises:
       executing an image analysis process on the data from the first set of data sources selected from the multiple data sources.

7. The method of claim 1, wherein:
   the configuration for the visual representations presentable on the display device corresponds to a phase-specific configuration associated with the current phase of the plurality of phases.

8. The method of claim 7, wherein:
   the phase-specific configuration defines a visibility of a visual representation corresponding to data from a data source of the multiple data sources.

9. The method of claim 1, wherein:
   the data from the first set of data sources selected from the multiple data sources comprise first data from a first data source of the first set of data sources and second data from a second data source of the first set of data sources, the first data comprising first positional information with respect to a common reference frame, and the second data comprising second positional information with respect to the common reference frame.

10. The method of claim 9, wherein:
    generating, based on at least the profile and determining that the current phase corresponds to the first phase, the first display configuration comprises:
        registering a first visual representation of the first visual representations corresponding to the first data and a second visual representation of the first visual representations corresponding to the second data based on the common reference frame;
        generating the first display configuration for the first visual representations based on at least the profile;
        determining that the current phase corresponds to the first phase; and registering the first visual representation and the second visual representation.

11. The method of claim 1, wherein:
the first display configuration is determined based on a user profile loaded prior to commencement of the surgical process, the user profile identifying an individual performing the surgical process and including user-preferences of the individual regarding organization of the visual representations corresponding to the data from the multiple data sources during different phases of the surgical process.

12. The method of claim 1, wherein:
generating, based on at least the profile and determining that the current phase corresponds to the first phase, the first display configuration for the first visual representations comprises:
generating the first display configuration for the first visual representations based on at least the profile, and
determining that the current phase corresponds to the first phase, and a user preference record.

13. The method of claim 12, wherein:
the user preference record is maintained as a user profile defined prior to commencement of the surgical process, the user profile comprising:
an identification of an individual performing the surgical process, and
a user preference associated with the individual, the user preference defining an organization of the first visual representations in the first display configuration.

14. A surgical system comprising:
a display device; and
one or more processing devices configured to perform operations comprising:
operating the surgical system to perform a surgical process comprising a plurality of phases;
determining that a current phase of the surgical process corresponds to a first phase of the plurality of phases;
generating, based on at least a profile and determining that the current phase corresponds to the first phase, a first display configuration for first visual representations corresponding to data from a first set of data sources selected from multiple data sources, the profile defining a configuration for visual representations presentable on the display device, wherein the configuration for the visual representations limits certain adjustments to a size of a view or prevents the view from being removed from the display device by a user, the configuration further defining a minimum size of the view presentable on the display device, the minimum size being defined by a safety condition specific to the current phase of the surgical process; and
presenting, on the display device, the first display configuration for the first visual representations.

15. The surgical system of claim 14, wherein:
the configuration for the visual representations presentable on the display device defines a visibility of a visual representation corresponding to data from a data source of the multiple data sources.

16. The surgical system of claim 14, wherein the operations further comprise:
determining that the current phase of the surgical process corresponds to a second phase of the plurality of phases;

generating, based on at least the profile and determining that the current phase corresponds to the second phase, a second display configuration for second visual representations corresponding to data from a second set of data sources selected from the multiple data sources; and
presenting, on the display device, the second display configuration for the second visual representations,
wherein the configuration corresponds to a first configuration associated with the first phase of the plurality of phases, and
wherein the profile defines a second configuration for the visual representations presentable on the display device, the second configuration associated with the second phase of the plurality of phases.

17. One or more machine-readable non-transitory storage devices encoded with machine-readable instructions configured to cause one or more processing devices to perform operations, the operations comprising:
operating a surgical system to perform a surgical process, the surgical system comprising a display device, and the surgical process comprising a plurality of phases;
determining that a current phase of the surgical process corresponds to a first phase of the plurality of phases;
generating, based on at least a profile and determining that the current phase corresponds to the first phase, a first display configuration for first visual representations corresponding to data from a first set of data sources selected from multiple data sources, the profile defining a configuration for visual representations presentable on the display device, wherein the configuration for the visual representations limits certain adjustments to a size of a view or prevents the view from being removed from the display device by a user, the configuration further defining a minimum size of the view presentable on the display device, the minimum size being defined by a safety condition specific to the current phase of the surgical process; and
presenting, on the display device, the first display configuration for the first visual representations.

18. The one or more machine-readable non-transitory storage devices of claim 17, wherein:
the configuration for the visual representations presentable on the display device defines a visibility of a visual representation corresponding to data from a data source of the multiple data sources.

19. The one or more machine-readable non-transitory storage devices of claim 17, wherein the operations further comprise:
determining that the current phase of the surgical process corresponds to a second phase of the plurality of phases;
generating, based on at least the profile and determining that the current phase corresponds to the second phase, a second display configuration for second visual representations corresponding to data from a second set of data sources selected from the multiple data sources; and
presenting, on the display device, the second display configuration for the second visual representations,
wherein the configuration corresponds to a first configuration associated with the first phase of the plurality of phases, and
wherein the profile defines a second configuration for the visual representations presentable on the display device, the second configuration associated with the second phase of the plurality of phases.

20. The method of claim 1, wherein the configuration for the visual representations causes an alert to be presented on the display device that indicates that adjustment of the size of the view has been limited or removal of the view has been prevented.

21. The surgical system of claim 14, wherein the configuration for the visual representations causes an alert to be presented on the display device that indicates that adjustment of the size of the view has been limited or removal of the view has been prevented.

22. The one or more machine-readable non-transitory storage devices of claim 17, wherein the configuration for the visual representations causes an alert to be presented on the display device that indicates that adjustment of the size of the view has been limited or removal of the view has been prevented.

\* \* \* \* \*